(12) United States Patent
Lang et al.

(10) Patent No.: US 6,592,895 B2
(45) Date of Patent: Jul. 15, 2003

(54) BIODEGRADABLE POLYHYDRIC ALCOHOL ESTERS

(75) Inventors: Meidong Lang, Shanghai (CN); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/194,965

(22) Filed: Jul. 15, 2002

(65) Prior Publication Data

US 2003/0109647 A1 Jun. 12, 2003

Related U.S. Application Data

(60) Provisional application No. 60/309,180, filed on Aug. 2, 2001.

(51) Int. Cl.$^7$ ............................ A61K 9/52; C08G 63/08
(52) U.S. Cl. ................. 424/457; 528/271; 528/272; 528/302; 528/354; 528/361; 525/437; 525/444; 424/426; 424/460; 424/461; 424/468
(58) Field of Search ................. 528/271, 272, 528/302, 354, 361; 525/437, 444; 424/426, 457, 460, 461, 468

(56) References Cited

U.S. PATENT DOCUMENTS 6,388,047 B1   5/2002   Won et al. ................. 528/354

FOREIGN PATENT DOCUMENTS

| WO | WO00/12619 | 3/2000 |
|----|------------|--------|
| WO | WO02/18477 | 3/2002 |

OTHER PUBLICATIONS

Lang, M., et al, J. Polym. Sci. Part A: Polym. Chem. 40, 1127–1141 (2002).

*Primary Examiner*—Samuel A. Acquah

(57) ABSTRACT

Precursor polyhydric alcohol esters where acyl moieties originate from aliphatic homopolymer or copolymer polyesters and contain free hydroxyl at their terminal ends, are reacted to provide 2-carboxy ethenyl groups. The resulting products can be used in formation of hydrogels for drug delivery or can be reacted to attach aminoxyl radical or drug molecule residue or other biologically active agent for delivery of these, for example, from vascular stents.

15 Claims, No Drawings

BIODEGRADABLE POLYHYDRIC ALCOHOL ESTERS

CROSS-REFERENCE TO RELATED APPLICATION

This application claims the benefit of U.S. Provisional Application No. 60/309,180 filed Aug. 2, 2001, the whole of which is incorporated by reference.

TECHNICAL FIELD

This invention is directed at biodegradable polyhydric alcohol esters where the acyl moieties originate from aliphatic homopolymer or copolymer polyesters.

BACKGROUND OF THE INVENTION

In recent years there has been an increased interest in star-shaped polymers, a kind of branched polymer having three or more polymeric arms attached to a center core.

This kind of polymer has not heretofore been used for biomedical application.

SUMMARY OF THE INVENTION

It has been discovered here that biodegradable star-shaped polymers useful inter alia for biomedical application can be made based on esterifying polyhydric alcohols to provide acyl moieties originating from aliphatic homopolymer or copolymer polyesters.

One embodiment of the invention herein, denoted the first embodiment, is directed to biodegradable polyhydric alcohol esters where the acyl moieties of the esters originate from aliphatic homopolymer or copolymer polyesters and contain free hydroxyl at their terminal ends and the weight average molecular weight of the esters ranges from 1,000 to 80,000, for example, from 2,000 to 50,000. These compounds are precursors for double bond functionalized biodegradable polyhydric alcohol esters where some or each of the acyl moieties are functionalized to incorporate an unsaturated group, which is another aspect of the invention herein. The functionalizing to incorporate unsaturated group can be effected, e.g., by reacting free hydroxyls with maleic anhydride to provide unsaturated terminal moieties which are 2-carboxy ethenyl groups.

Another embodiment of the invention herein, denoted the second embodiment, is directed to biodegradable polyester-polysaccharide hydrogels formed by photocrosslinking esters of polysaccharide formed by reaction of polysaccharide with hydroxy function pendant groups, for example, unsaturated esters of polysaccharide formed by reaction of polysaccharide with unsaturated group providing compound, with 2-carboxy ethenyl terminated polyhydric alcohol esters of the first embodiment. These hydrogels are useful, for example, as drug delivery systems.

The weight average molecular weights herein are determined by gel permeation chromatography using polystyrene standards.

The term "photocrosslinking" is used herein to mean causing vinyl bonds to break and form cross-links by the application of radiant energy.

The term "biodegradable" is used herein to mean capable of being broken down by various enzymes such as trypsins, lipases and lysosomes in the normal functioning of the human body and living organisms (e.g., bacteria) and/or water environment.

DETAILED DESCRIPTION

We turn now to the compounds of the first embodiment which are biodegradable polyhydric alcohol esters where the acyl moieties of the esters originate from aliphatic homopolymer or copolymer polyesters and contain free hydroxyl at their terminal ends and the weight average molecular weight of the esters ranges from 1,000 to 80,000, for example, from 2,000 to 50,000.

The polyhydric alcohol moiety portion of the polyhydric alcohol esters is obtained by action of the acid group of aliphatic homopolymer or copolymer polyester on a polyhydric alcohol having, for example, from 3 to 6 hydroxyl groups. The aliphatic homopolymer or copolymer polyesters include, for example, poly($\epsilon$-caprolactone) which can be formed in situ during the esterification reaction and which is preferred herein, poly(lactide-co-$\epsilon$-caprolactone) which can be formed in situ during the esterification reaction, poly(glycolide-co-$\epsilon$-caprolactone) which can be formed in situ during the esterification reaction, poly($\beta$-valerolactone-co-$\epsilon$-caprolactone) which can be formed in situ during the esterification reaction, poly($\beta$-hydroxybutyrate-co-$\epsilon$-caprolactone) which can be formed in situ during the esterification reaction, and poly(1,4-dioxan-2-one-co-$\epsilon$-caprolactone) which can be formed in situ during the esterification reaction. The polyhydric alcohols include, for example, glycerol, glycerol derivatives, pentaerythritol, sugars, e.g., glucose and glucono-$\delta$-lactone; 1,3-propanediol-2-ethyl-2-(hydroxymethyl); butanediols, D-+-arabitol, perseitol ribitol, xylitol, D-threitol, dulcitol L-fucitol sorbitol, erythritol, dextran and other polysaccharides, and polyvinyl alcohol.

The maximum number of polymeric arms obtained in the polyhydric alcohol esters of the first embodiment corresponds to the number of hydroxyl groups on the polyhydric alcohol.

We turn now to the case where the acyl moieties originate from poly($\epsilon$-caprolactone) which is formed in situ during the esterification reaction. The polyhydric alcohol esters are obtained by a ring opening polymerization of $\epsilon$-caprolactone in the presence of the polyhydric alcohol. The mole ratio of $\epsilon$-caprolactone to hydroxyl of polyhydric alcohol ranges from 1:1 to 150:1. Thus, for example, in the case of glycerol as the polyhydric alcohol, the mole ratio is calculated from three times the moles of $\epsilon$-caprolactone per mole of glycerol; and in the case of pentaerythritol, the mole ratio is calculated from four times the moles of $\epsilon$-caprolactone per mole of pentaerythritol.

The esterification reaction is preferably carried out in the presence of a ring opening catalyst, e.g., stannous octoate, present in an amount ranging from 0.01% by weight to 1% by weight of $\epsilon$-caprolactone. Ring opening catalysts that can be used in place of stannous octoate include, for example, aluminum triisopropoxide, [(n-$C_4H_9O)_2AlO]_2Zn$, dibutyltin dimethoxide, Zn L-lactate, aluminum thiolates and triethyl aluminum.

The esterification reaction is carried out, for example, at 20 to 150° C. for 10 minutes to 72 hours in a polymerization tube containing dry inert gas (e.g., argon or nitrogen) sealed in vacuum. The inclusion of the dry inert gas prevents hydrolysis and oxidation of the catalyst.

The structure of a three-arm polyhydric alcohol ester obtained from ring opening polymerization of $\epsilon$-caprolactone in the presence of glycerol is depicted below:

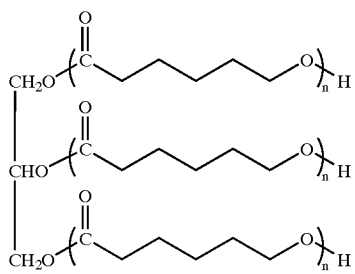

In the above structure, n ranges, for example, from 1 to 150.

The structure of a four-arm polyhydric alcohol ester obtained from ring opening polymerization of ε-caprolactone in the presence of pentaerythritol is depicted below:

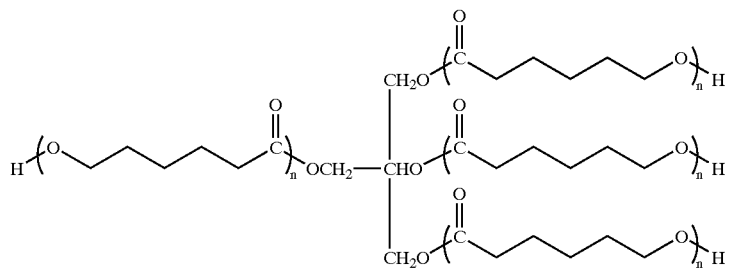

In the above structure, n ranges, for example, from 1 to 150.

As indicated above, the polyhydric alcohol esters containing free hydroxyl at terminal ends of the acyl moieties are precursors for double bond functionalized biodegradable polyhydric alcohol esters where some or each of the acyl moieties are functionalized to incorporate an unsaturated group. In a preferred case, the functionalizing is obtained by reaction of free hydroxyls of the precursor compounds with maleic anhydride. Other reactants besides maleic anhydride to incorporate unsaturated group include, for example, acryloyl chloride which is $CH_2=CHCOCl$, methacryloyl chloride which is $CH_2=CH(CH_3)COCl$ and allyl isocyanate which is $CH_2=CHCH_2NCO$. In the case where maleic anhydride is utilized, unsaturated terminal moieties are obtained which are 2-carboxy ethenyl groups.

For the reaction of maleic anhydride with free hydroxyl at terminal end of acyl moiety of precursor free hydroxyl containing polyhydric alcohol ester, the mole ratio of hydroxyl functionality to moles of maleic anhydride can range, for example, from 1:1 to 1:10, and the reaction can be carried out at 100 to 180° C. over a time period of 1 hour to 72 hours and preferably is carried out under inert gas such as nitrogen to prevent hydrolysis of maleic anhydride and of the precursor esters. The reaction with maleic anhydride produces 2-carboxy ethenyl functionalized maximum number of arms corresponding to number of free hydroxyls on polyhydric alcohol starting material, hereinafter referred to as 2-carboxy ethenyl functionalized polyhydric alcohol esters.

A structure of a 2-carboxy ethenyl functionalized polyhydric alcohol ester obtained from precursor obtained from glycerol is depicted below:

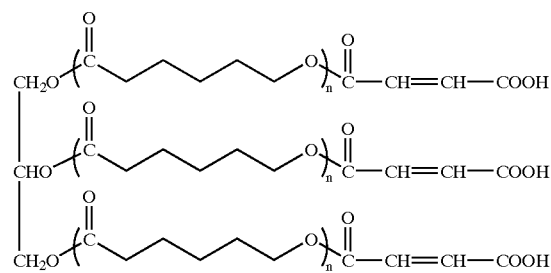

In the above structure, n can range, for example, from 1 to 150.

A structure of a 2-carboxy ethenyl functionalized polyhydric alcohol ester obtained from precursor obtained from pentaerythritol is depicted below:

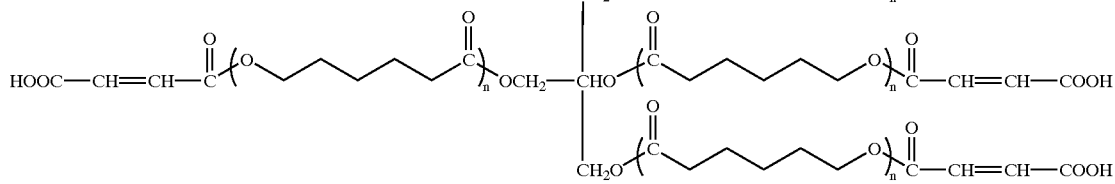

In the above structure, n can range, for example, from 1 to 150.

Biological and material properties of the esters can be varied by varying the feed ratio of ε-caprolactone to polyhydric alcohol to change the molecular weight of the precursor polyhydric alcohol.

The functionalized poly(ε-caprolactone) arms of the functionalized polyhydric alcohol esters herein are biodegradable as said arms are hydrolyzed even in enzyme free water and hydrolases, e.g., trypsin and lipases, which are present biologically, catalyze the hydrolysis.

The double bond functionalized polyhydric alcohol esters herein can be photocrosslinked by dissolving to form a solution, adding photoinitiator, e.g., 2,2'-dimethoxy-2-phenyl acetophenone or other photoinitiator (e.g., 1 to 5%, e.g., 4%, photoinitiator by weight of ester), forming a film and irradiating with a long wave UV lamp, e.g., a 365 nm long wave UV lamp, for 5 hours. The formed three dimensional structures can be used to entrap drugs to provide slow release drug delivery systems.

The 2-carboxy ethenyl functionalized polyhydric alcohol esters are also useful to form biodegradable polyester-polysaccharide hydrogels.

2-Carboxy ethenyl functionalized polyhydric alcohol ester and reaction product of polysaccharide are photocrosslinked in solution to provide the biodegradable polyester-polysaccharide hydrogels. Photoinitiator and irradiation means for the photocrosslinking can be the same as described above for photocrosslinking. The resulting hydrogel is biodegradable (a biodegradable hydrogel is a hydrogel formed by cross-linking a polymer which is degraded by water and/or by enzymes found in nature).

Polysaccharides useful to prepare reaction product for photocrosslinking with 2-carboxy ethenyl functionalized polyhydric alcohol, have hydroxy function pendant groups which permit the formation of a three dimensional network. These polysaccharides include, for example, dextran, inulin, starch, cellulose, pullan, levan, mannan, chitin, xylan, pectin, glucuronan, laminarin, galactomannan, amylose, amylopectin, and phytophtoorglucans. A preferred polysaccharide is dextran.

In the case of 2-carboxy ethenyl functionalized polyhydric alcohol polyester being used to form biodegradable polyester-dextran reaction product hydrogels, dextran having a weight average molecular weight ranging from 40,000 to 80,000 (dextran is (1→6) linked α-D-glucopyranosyl residues and carries three hydroxyl groups per glucose unit) is photocrosslinked with 2-carboxy ethenyl functionalized polyhydric alcohol ester. The reaction to form the dextran reaction product is readily carried out in an aprotic solvent, e.g., dimethyl formamide or dimethyl sulfoxide, and is catalyzed by a Lewis-base, preferably triethylamine. A preferred dextran reaction product is dextran maleic acid monoester prepared as described in WO 00/12619.

The resulting hydrogel is useful to entrap or be covalently bonded to drug or other biologically active agent for a slow release drug delivery system. The same method for entrapping drug can be used as is described in conjunction with indomethacin as drug and a different hydrogel in WO 00/60956, published Oct. 19, 2000. Utilities for the hydrogel here include those described in WO 00/60956 for the hydrogel there. In particular, the hydrogel can be tailored to provide drug control release, wound coverage, skin substitutes, delivery of viruses in gene therapy, coatings for surgical implants (e.g., an artificial pancreas) including a vascular (e.g., a cardiac) stent, and coatings for tissue culture plates to promote cell adhesive and proliferation.

For a case where the 2-carboxy ethenyl functionalized polyhydric alcohol esters can be used independent of forming a hydrogel the 2-carboxy ethenyl functionalized polyhydric alcohol esters can be polymerized with unsaturated monomers, e.g., acrylic acid, methacrylic acid or maleic anhydride, by free radical polymerization to link polyacrylic or polymethacrylic or polymaleic acid segment to replace each carboxyl with a plurality of carboxyls for attachment of moieties containing aminoxyl-containing radical or other drug molecule residue or other biologically active agent residue in place of hydroxyl moiety of carboxyl group. The reaction is carried out under free radical polymerization conditions. The reaction is initiated using 2,2'-azobisisobutyronitrile (AIBN) or other initiator agent and can be carried out in dioxane with heating to 60° C. for 5 hours.

We turn now to attachment of moiety containing aminoxyl-containing radical or other drug molecule residue or other biologically active agent residue in place of hydroxyl moiety of carboxyl group.

Reaction to include an aminoxyl-containing radical can be carried out by reacting spin label suitable to replace hydroxy in carboxyl with imino linked to the four position of 2,2,6,6-tetramethylpiperidine-1-oxy or with imino linked to the three position of 2,2,5,5-tetramethylpiperidine-1-oxy or with oxy linked to the carbonyl of 2,2,5,5-tetramethyl-3-pyrroline-1-oxy-3-carbonyl. Suitable spin labels are listed in U.S. Pat. No. 5,516,881. The term "aminoxyl" is used herein to refer to the structure >N-O. The term "aminoxyl-containing radical" is used herein to refer to a radical that contains the structure >N-O. The products are useful for aminoxyl radical treatment of tumors, and to increase the efficiency of chemotherapy and ionizing radiation therapy of tumors and for the reconstruction of injured, diseased, or aged human blood vessels and as an approach to controlling, neutralizing and reducing the excess of naturally formed nitric oxide.

Reaction to include other drug molecule residue or other biologically active agent residue in place of the hydroxyl moiety of carboxyl group can be carried out by reacting the other drug or biologically active agent with group(s) thereon reactable with carboxyl group to attach other drug molecule residue or other biologically active agent via ester, amide or oxycarbonyl linkage or carboxylate via ionic bond. Other drugs and other biologically active agents with groups thereon reactable with carboxyl group include other drugs or other biologically active agents containing an amine group or oxy linked to carbonyl or carboxylate or carboxylic acid or which are modified to contain such group, e.g., estrone, estradiol, doxorubicin or camptothecin.

Uses of the products in the case of 2-carboxy ethenyl functionalized polyhydric alcohol esters polymerized with unsaturated monomers, e.g., acrylic acid, methacrylic acid or maleic anhydride with hydroxyl in carboxyl replaced with moiety containing aminoxyl-containing radical or other drug molecule residue or other biologically active agent residue, include drug and other biologically active agent control/release devices including drug or biologically active agent eluting polymer coating systems for coating vascular stents (e.g., cardiac stents) or other devices and as scaffolds for tissue engineering.

The biodegradable polyester-polysaccharide hydrogels and 2-carboxy ethenyl functionalized polyhydric alcohol esters polymerized with unsaturated monomers can also be admixed with spin labels and other drugs and biologically active agents to provide drug delivery matrixes.

Controlled release functionality including sustained or delayed release functionality via direct covalent bonding or ionic bonding, of the aminoxyl-containing radical or other drug or other biologically active agent can be obtained, by various conjugation techniques using different molecule lengths and structure via spacer molecules to conjugate spin label of other drug or other biologically active agent to polymer backbone; or a polymer drug matrix can be created by admixing spin label or other drug or other biologically active agent with the polymeric component; or strata of drugs and polymeric materials can be structured in layers; or a topcoat can be applied using various hydrogel/drug mixtures to obtain a controlled, sustained drug release local delivery system. These can be provided, for example, on a stent platform, or on a microphere (nanoparticle) to provide a microphere based drug delivery system for systemic application.

We turn now to the cases where the polyhydric alcohol esters herein are used for providing drug/other biologically active release coatings on vascular stents e.g., cardiac stents. As indicated above, one case of this is where the polyhydric alcohol esters herein are used to form hydrogels entrapping or covalently bonded to drug or other biologically active agent. As indicated above, another case is where 2-carboxy ethenyl functionalized polyhydric alcohol ester is reacted with acrylic acid or methacrylic acid or maleic anhydride in a free radical polymerization followed by attachment of aminoxyl containing radical or other drug molecule or other biologically active agent.

The therapeutic agents which are used in association with products from polyhydric alcohol esters herein for drug/biologically active release coatings on stents include small molecules; e.g., weight average molecular weight ranging from 200 to 1,000, including for example, indomethacin, hypoestoxide, paclitaxel and other taxane derivatives, sirolimus, dexamethasone, trazolopyrimidine, tranilast, thalidomide and its analogs and simvastatin and other statin analogs, and large molecules, e.g., weight average molecular weight of 1,000 to 100,000, including, for example antisense oligo nucleotides (e.g., anti-sense oligo nucleotide with morpholine based backbone which is sold under the name NEU-GENES® which has limited water solubility), gene products (e.g., Ad5-FGF4 Gene for angiogenesis named GENERX® and described in Circulation, Mar. 19, 2002), two cell cycle inhibitory genes p27 and p 16 as described in tctmd.com, Aug. 16, 2001, and antibodies and antibody fragments (e.g., c7E3 Fab denoted ABCIXIMAB® for anti-platelet use, described in Baron, J., et al, Cardiovascular Res 48, 464–472, 2000).

In the case where hydrogel is coated on a stent, this can be carried out, for example, by coating solution of hydrogel forming agents plus drug on the stent and forming the hydrogel on the stent or by forming dry-to-the-touch hydrogel associated with drug and adhering this to the stent.

In the case where 2-carboxy ethenyl functionalized polyhydric alcohol is reacted with acrylic acid or methacrylic acid in free radical polymerization followed by attachment of or matrixing with drug, attachment of the product to stent may be carried out by dip coating, e.g., from a solution.

The drug is used on the stent or other device in a therapeutically effective amount. The therapeutically effective amount of the therapeutic agent is that amount which accomplishes the purpose for which the therapeutic agent is present on the stent or other device, e.g, an anti-inflammation effecting amount for an anti-inflammatory agent, a cholesterol reducing or HDL increase causing amount for an anti-cholesterol agent, a platelet formation inhibiting amount for an antiplatelet agent, a reocclusion ameliorating or preventing amount for agents administered for this purpose, an immune suppression effecting amount to prevent stent rejection and an angiogenesis causing amount for an angiogenesis promoting agent.

In both of the above cases, attachment can be directly onto a vascular stent or to a polymer coated vascular stent or as a topcoat on a stent over other biodegradable polymer coating (e.g., poly ester-amide with covalently congregated matrixed drugs).

The term "drug" is used herein to mean a substance for use in the diagnosis, cure, mitigation, treatment or prevention of disease. Typically, drugs have weight average molecular weights ranging from 200 to 1,000. The word "other" in the term "other drugs" is used herein to mean the drug does not contain a group containing the aminoxyl structure.

The term "other biologically active agent" is used herein to include proteins, cytokines, oligo nucleotides including antisense oligo nucleotides, genes, carbohydrates and hormones, but excludes compounds containing an aminoxyl containing radical and "other drug molecule."

The term "residue" in other drug molecule residue and other biologically active agent residue connotes the other drug molecule or other biologically active agent minus any portion thereof separated on attachment in the reaction referred to.

We turn now to the case of polyhydric alcohol esters where the acyl moieties originate from poly(lactide-co-$\epsilon$-caprolactone), e.g., having a weight average molecular weight ranging from about 750 to 150,000, which is formed in situ during the esterification reaction. Preparation can be carried out in this case by substituting a blend of lactide and $\epsilon$-caprolactone monomers for the $\epsilon$-caprolactone monomer in the preparation described above for the case where the acyl moieties originate from poly($\epsilon$-caprolactone) homopolymer which is formed in situ during the esterification reaction with polyhydric alcohol.

We turn now to the case of polyhydric alcohol esters where the acyl moieties originate from poly(glycolide-co-$\epsilon$-caprolactone), e.g., having a weight average molecular weight ranging from 750 to 150,000 which is formed in situ during the esterification reaction. Preparation can be carried out in this case by substituting a blend of glycolide and $\epsilon$-caprolactone monomers for the $\epsilon$-caprolactone monomer in the preparation described above for the case where the acyl moieties originate from poly($\epsilon$-caprolactone) homopolymer which is formed in situ during the esterification reaction with polyhydric alcohol.

Similar preparations to what are described in the above two paragraphs are appropriate in the case of polyhydric alcohol esters where the acyl moieties originate from poly($\delta$-valerolactone-co-$\epsilon$-caprolactone), poly($\beta$-hyroxybutyrate-co-$\epsilon$-caprolactone) and poly(1,4-dioxan-2-one-co-$\epsilon$-caprolactone).

In the cases for polyhydric alcohol esters where acyl moieties originate from poly(lactide-co-$\epsilon$-caprolactone) or poly(glycolide-co-$\epsilon$-caprolactone), or poly($\delta$-valerolactone-co-$\epsilon$-caprolactone, or poly($\beta$-hyroxybutyrate-co-$\epsilon$-caprolactone) or poly(1,4-dioxan-2-one-co-co-$\epsilon$-caprolactone), free hydroxyl can be converted to 2-carboxy ethenyl by reaction with maleic anhydride under conditions as described in U.S. application Ser. No. 10/101,408, filed on Mar. 20, 2002. The 2-carboxy ethenyl groups can be converted to poly(meth)acrylic acid segments as described in U.S. application Ser. No. 10/101,408.

The utilities for the case for polyhydric alcohol esters where the acyl moieties originate from poly(lactide-co-$\epsilon$-caprolactone) or poly(glycolide-co-$\epsilon$-caprolactone) or poly($\delta$-valerolactone-co-$\epsilon$-caprolactone) or poly($\beta$-hyroxybutyrate-co-$\epsilon$-caprolactone) or poly(1,4-dioxan-2-one-co-$\epsilon$-caprolactone) or other polyesters, e.g., carboxy ethenyl (maleic acid functionalized) dextran, are the same as in the case where the acyl moieties originate from polymerization of $\epsilon$-caprolactone.

The utilities are the same as in the cases where the alcohol moiety is obtained from glycerol and pentaerythritol for the cases where the alcohol moiety is obtained from other polyhydric alcohols as described hereinbefore including dextran and other polysaccharides.

The invention is illustrated by the following working examples:

EXAMPLE I

Runs were carried out as follows to prepare glycerol esters where the acyl moieties of the esters are from poly (ε-caprolactone) and are hydroxyl functionalized, by ring opening polymerization of ε-caprolactone in the presence of glycerol:

Glycerol (0.02 moles), ε-caprolactone (0.10 moles) and stannous octoate (0.1% by weight of the ε-caprolactone) were added into a silanized polymerization tube (feed molar ratio of ε-caprolactone (CL) to hydroxyl (OH) of glycerol was 5:1). This was followed by argon-filling of head space for several times whereupon the polymerization tube was sealed under vacuum. The sealed tube was placed in an oil bath at 130° C. and maintained there for 48 hours to cause ring opening polymerization of ε-caprolactone in the presence of the glycerol to obtain the glycerol esters where the acyl moieties of the esters are each from poly (ε-caprolactone) and are hydroxyl functionalized, denoted PGCL-OH. The sealed tube was removed from the oil bath and cooled to room temperature, whereupon the raw product was removed from the polymerization tube by dissolving in chloroform. The resulting solution was poured into excess petroleum ether to precipitate the product. The precipitate was washed with distilled water four times and dried over $P_2O_5$ under vacuum at room temperature until constant weight was obtained. The product was denoted PGCL-OH-1.

Other runs were carried out as above except that the feed molar ratios of ε-caprolactone to hydroxyl of glycerol were 10:1, 20:1 and 40:1, and the products were respectively denoted PGCL-OH-2, PGCL-OH-3 and PGCL-OH-4.

The yields, number average molecular weights $M_n$, weight average molecular weights $M_w$, peak molecular weights $M_p$ (the weight average molecular weights at the peaks of the GPC curves for the samples) and polydispersities $M_w/M_n$ are given in Table 1 below. $M_n$, $M_w$ and $M_p$ were determined by gel permeation chromatography using polystyrene standards.

TABLE 1

| Sample No. | Feed molar ratio (CL/OH) | Yield (%) | $M_n$ (×10³) | $M_w$ (×10³) | $M_p$ (×10³) | poly-dispersity ($M_w/M_n$) |
|---|---|---|---|---|---|---|
| PGCL-OH-1 | 5/1 | 93.2 | 2.50 | 3.74 | 3.92 | 1.49 |
| PGCL-OH-2 | 10/1 | 95.9 | 6.28 | 9.69 | 10.6 | 1.54 |
| PGCL-OH-3 | 20/1 | 95.9 | 15.4 | 25.8 | 22.5 | 1.68 |
| PGCL-OH-4 | 40/1 | 94.3 | 18.9 | 29.0 | 30.3 | 1.54 |

Runs were carried out as follows to convert the esters of Table 1 to 2-carboxy ethenyl functionalized polyhydric alcohol esters.

PGCL-OH-1 (0.01 moles) of that made above and 5 equivalents of maleic anhydride per hydroxyl of PGCL-OH-1 were placed in a three-neck flask under $N_2$ atmosphere and maintained at 130° for 24 hours. The reaction mixture was then cooled to room temperature and dissolved in chloroform. The resulting chloroform solution was poured into excess petroleum ether to precipitate product. The precipitate was stirred in 500 ml of distilled water for four hours to remove excess maleic anhydride. After filtration, the precipitate was washed with distilled water four times and dried over $P_2O_5$ under vacuum at room temperature until constant weight was obtained. The product was denoted PGCL-Ma-1.

Other runs were carried out as in the above paragraph except that equal molar amounts of PGCL-OH-2, PGCL-OH-3 and PGCL-OH-4 were substituted for the PGCL-OH-1. The products were respectively denoted PGCL-Ma-2, PGCL-Ma-3 and PGCL-Ma-4.

The number average molecular weights and polydispersities (determined by gel permeation chromatography using polystyrene standards) for the products PGCL-Ma-1, PGCL-Ma-2, PGCL-Ma-3 and PGCL-Ma-4 are given in Table 2 below:

TABLE 2

| Sample No. | $M_n$ (×10³) | polydispersity ($M_w/M_n$) |
|---|---|---|
| PGCL-Ma-1 | 2.42 | 2.75 |
| PGCL-Ma-2 | 5.62 | 1.85 |
| PGCL-Ma-3 | 13.3 | 1.85 |
| PGCL-Ma-4 | 16.1 | 1.71 |

Runs were carried out as follows to convert the products of Table 2 to produce crosslinked films:

PGCL-Ma-1 (1 gram) was dissolved in dioxane (5% wt./vol.). The photoinitiator, 2,2'-dimethoxy-2-phenyl acetophenone (4% by weight of the PGCL-Ma-1) was added to the solution and dissolved on rapid stirring for a few minutes. The solution was poured onto a glass plate and irradiated with 365 nm long wave UV lamp (Model UVL-18, 8 watt handheld, UVP, Upland, Calif., USA) for 5 hours. The resulting crosslinked film was dried in a vacuum oven at room temperature. The product was an opaque film and was denoted NPGCL-Ma-1.

Other runs were carried out as in the above paragraph except that equal molar amounts of PGCL-Ma-2, PGCL-Ma-3 and PGCL-Ma-2 were substituted for the PGCL-Ma-1. The products were opaque films and were respectively denoted NPGCL-Ma-2, NPGCL-Ma-3 and NPGCL-Ma-4.

Whereas PGCL-Ma-1, PGCL-Ma-2, PGCL-Ma3 AND PGCL-Ma-4 dissolved in ethyl acetate, dioxane, chloroform, tetrahydrofuran, methyl sulfoxide, N,N-dimethyl formamide, dichloromethane and acetone, the crosslinked products NPGCL-Ma-1, NPGCL-Ma-2, NPGCL-Ma-3 and NPGCL-Ma-4, did not.

A comparison of melting temperatures, heats of fusion and degrees of crystallinity for PGCL-Ma-1, PGCL-Ma-2; PGCL-Ma-3 and PGCL-Ma-4 to those for NPGCL-Ma-1, NPGCL-Ma-2, NPGCL-Ma-3 and NPGCL-Ma-4 is given in Table 3 below. Melting temperatures were measured using a differential scanning calorimeter (DSC), Perkin-Elmer DSC-7 under nitrogen purging at a heating rate of 10° C./minute from −50° to 120°. Each PGCL-Ma sample had one endothermic peak that split to two melting peaks while each corresponding NPGCL-Ma product had an endothermic peak that did not split. The heats of fusion $\Delta H_m$, were determined by integrating the normalized area of melting endotherms. The degree of crystallinity in each case equals the $\Delta H_m$ for the sample divided by the $\Delta H_m$ for 100% crystalline times 100.

TABLE 3

| Sample No. | $T_m$ (° C.) | $\Delta H_m$ (J/g) | $X_c$ (%) |
|---|---|---|---|
| PGCL-Ma-1 | 39.3, 44.9 | 64.9 | 48.1 |
| PGCL-Ma-2 | 45.9, 51.3 | 73.6 | 54.5 |
| PGCL-Ma-3 | 54.5, 56.2 | 85.9 | 63.6 |
| PGCL-Ma-4 | 55.4, 58.2 | 87.5 | 64.8 |
| NPGCL-Ma-1 | 37.2 | 48.1 | 35.6 |
| NPGCL-Ma-2 | 47.2 | 50.8 | 37.6 |
| NPGCL-Ma-3 | 53.7 | 66.3 | 49.1 |
| NPGCL-Ma-4 | 56.2 | 73.3 | 54.3 |

In the above Table 3, $T_m$ is the melting temperature determined as described above, $\Delta H_m$ is the heat of fusion determined as described above and $\chi_c$ is the degree of crystallinity. As indicated in Table 3, the melting points, heats of fusion and degrees of crystallinity decreased after crosslinking.

EXAMPLE II

Runs were carried out as follows to prepare pentaerythritol esters where the acyl moieties of the esters are from poly (ε-caprolactone) and are hydroxyl functionalized, by ring opening polymerization of ε-caprolactone in the presence of pentaerythritol.

Pentaerythritol (0.02 moles), ε-caprolactone (0.1 moles) and stannous octoate (0.1% by weight of the ε-caprolactone) were added into a silanized polymerization tube (feed molar ratio of ε-caprolactone (CL) to hydroxyl (OH) of pentaerythritol was 5:1). This was followed by argon-filling of head space for several times whereupon the polymerization tube was sealed under vacuum. The sealed tube was placed in an oil bath at 130° and maintained there for 48 hours to cause ring opening polymerization of ε-caprolactone in the presence of the pentaerythritol to obtain the pentaerythritol esters when the acyl moieties of the esters are each from poly(ε-caprolactone) and are hydroxyl functionalized, denoted PPCL-OH. The sealed tube was removed from the oil bath and cooled to room temperature, whereupon the raw product was removed from the polymerization tube by dissolving in chloroform. The resulting solution was gently poured into excess petroleum ether to precipitate product. The precipitate was obtained by filtering and then was dried. The powder precipitate was washed with distilled water four times and dried over $P_2O_5$ under vaccum at room temperature until constant weight was obtained. The product was denoted PPCL-OH-1.

Other runs were carried out the same as in the above paragraph except that the feed molar ratios of ε-caprolactone to hydroxyl of pentaerythritol were 10:1, 20:1 and 40:1, and the products were respectively denoted PPCL-OH-2, PPCL-OH-3 and PPCL-OH-4.

The yields, number average molecular weights $M_n$, weight average molecular weights $M_w$, peak molecular weights $M_p$ (the weights average molecular weights at the peaks of the GPC curves for the samples) and polydispersities $M_w/M_n$ are given in Table 4 below. $M_n$, $M_w$ and $M_p$ were determined by gel permeation chromatography using polystyrene standards.

TABLE 4

| Sample No. | Feed molar ratio (CL/OH) | Yield (%) | $M_n$ (×10³) | $M_w$ (×10³) | $M_p$ (×10³) | Polydispersity ($M_w/M_n$) |
|---|---|---|---|---|---|---|
| PPCL-OH-1 | 5/1 | 95.7 | 4.29 | 5.99 | 6.07 | 1.40 |
| PPCL-OH-2 | 10/1 | 96.9 | 7.23 | 10.6 | 11.0 | 1.45 |
| PPCL-OH-3 | 20/1 | 64.4 | 17.3 | 24.1 | 24.3 | 1.39 |
| PPCL-OH-4 | 40/1 | 28.90 | 28.9 | 41.3 | 40.5 | 1.43 |

The relationship of the feed molar ratios and the residual hydroxyls of pentaerythritol in PPCL-OH is given in Table 5 shown below:

TABLE 5

| Sample No. | Feed molar ratio (CL/OH) | Residual hydroxyls pentaerythritol (%) |
|---|---|---|
| PPCL-OH-1 | 5/1 | 28.8 |
| PPCL-OH-2 | 10/1 | 23.9 |
| PPCL-OH-3 | 20/1 | 19.1 |
| PPCL-OH-4 | 40/1 | 7.3 |

Runs were carried out as follows to convert the esters of Table 4 to 2-carboxy ethenyl functionalized polyhydric alcohol esters.

PPCL-OH-1 (0.01 moles) of that made above and 5 equivalents of maleic anhydride per hydroxyl of PPCL-OH-1 were placed in a round bottomed three-neck flask under $N_2$ atmosphere at 130°, and continuous stirring of the melt was carried out for 24 hours. After reaction for 24 hours, the reaction mixture was cooled at room temperature and dissolved in chloroform. The chloroform solution was gently poured into six times volume of petroleum ether to precipitate product. The precipitate was stirred in 500 ml of distilled water for four hours to remove any excess maleic anhydride. After filtration, the precipitate was washed four times with distilled water and dried over $P_2O_5$ under vacuum at room temperature until constant weight was obtained. The product was denoted PPCL-Ma-1.

Other runs were carried out as in the above paragraph except that equal molar amounts of PPCL-OH-2, PPCL-OH-3 and PPCL-OH-4 were substituted for the PPCL-OH-1. The products were respectively denoted PPCL-Ma-2, PPCL-Ma-3 and PPCL-Ma-4.

The number average molecular weights and polydispersities (both determined by gel permeation chromatography using polystyrene standards) for the products PPCL-Ma-1, PPCL-Ma-2, PPCL-Ma-3 and PPCL-Ma-4 are given in Table 6 below.

TABLE 6

| Sample No. | $M_n$ (×10³) | polydispersity ($M_w/M_n$) |
|---|---|---|
| PPCL-Ma-1 | 3.52 | 2.27 |
| PPCL-Ma-2 | 5.11 | 2.67 |
| PPCL-Ma-3 | 9.51 | 2.86 |
| PPCL-Ma-4 | 11.7 | 2.94 |

Quantitative conversion of hydroxyl functionality of the residual hydroxyls of pentaerythritol as well as the end hydroxys of the poly (ε-caprolactone) occurred at lower molecular weights, namely for sample PPCL-Ma-1.

Crosslinking of the PPCL-Ma samples was carried out as follows. The double bond functionalized product PPCL- Ma-1 (1 gram) was dissolved in dioxane (5% wt./vol). The photoinitiator 2,2'-dimethoxy-2-phenyl acetophenone (4% by weight of PPCL-Ma-1) was added to the solution and rapid stirring was carried out for a few minutes to facilitate dissolution of the initiator. The resulting solution was poured into a glass plate and the layer on the plate was irradiated with a 365 mm long wave UV lamp (Model UVL-18, 8 watt, handheld, UVP, Upland, Calif., USA) for 5 hours. The resulting cross linked film was dried in a vacuum oven at room temperature. The product was an opaque film and was denoted NPPCL-Ma-1.

Other runs were carried out as in the above paragraph except that equal molar amounts of PPCL-Ma-2, PPCL-Ma-3 and PPCL-Ma-4 were substituted for the PPCL-Ma1. The products were opaque films and were respectively denoted NPPCL-Ma-2, NPPCL-Ma-3 and NPPCL-Ma-4.

Whereas PPCL-Ma-1, PPCL-Ma-2, PPCL-Ma-3 and PPCL-Ma-4 dissolved in ethyl acetate, dioxane, chloroform, tetrahydrofuran, methyl sulfoxide, N,N-dimethyl formamide, dichlormethane and acetone, NPPCL-Ma-1, NPPCL-Ma-2, NPPCL-Ma-3 and NPPCL-Ma-4 did not.

A comparison of melting temperatures, heats of fusion and degrees of crystallinity for PPCL-Ma-1, PPCL-Ma-2, PPCL-Ma-3 and PPCL-Ma-4 to those of NPCCL-Ma-1, NPPCL-Ma-2, NPPCL-Ma-3 and NPPCL-Ma-4 are given in Table 7 below. Melting temperatures were measured using a differential scanning calorimeter (TA Instruments, DSC 2920) under nitrogen purging at a heating rate of 10° C./minute from −50° to 120° C. Each PPCL-Ma sample bad one endothermic peak that split to two melting peaks, while corresponding NPCC-Ma products bad one endothermic peak that did not split. The heat of fusion $\Delta H_m$ in each case was determined by integrating the normalized area of melting endotherm. The degree of crystallinity in each case equals the $\Delta H_m$ for the sample divided by $\Delta H_m$ for 100% crystalline times 100.

TABLE 7

| Sample No. | $T_m$ (° C.) | $\Delta H_m$ (J/g) | $X_c$ (%) |
|---|---|---|---|
| PPCL-Ma-1 | 22.8, 34.0 | 43.4 | 32.1 |
| PPCL-Ma-2 | 44.9, 49.9 | 71.7 | 53.1 |
| PPCL-Ma-3 | 50.7, 54.9 | 79.8 | 59.1 |
| PPCL-Ma-4 | 53.9, 56.4 | 81.0 | 60.3 |
| NPPCL-Ma-1 | 34.1 | 0.04 | 0 |
| NPPCL-Ma-2 | 43.5 | 24.3 | 18.0 |
| NPPCL-Ma-3 | 49.9 | 61.8 | 45.8 |
| NPPCL-Ma-4 | 54.6 | 61.6 | 45.6 |

In the above Table 7, $T_m$ is the melting temperature determined as described above, $\Delta H_m$ is the heat of fusion determined as described above and $\chi_c$ is the degree of crystallinity. The melting temperature for each PPCL-Ma sample decreased after crosslinking. The heat of fusion of each PPCL-Ma sample decreased after crosslinking. The degree of crystallinity of each PPCL-Ma sample decreased after crosslinking.

EXAMPLE III

PGCL-Ma-3 is dissolved in dimethyl formamide to provide a concentration of 5% w/v. Then 2,2'-dimethoxy-2-phenyl acetophenone is added as photoinitiator (4% by weight of PGCL-Ma-3). Then directly before crosslinking, 2.5% indomethacin (w/w based on the weight of PGCL-Ma-3) is added. The resulting composition is poured onto glass plates and irradiated with 365 nm long wave UV lamp for 5 hours. The resulting crosslinked film entrapping indomethacin is dried in a vacuum oven at room temperature.

In another case an equal molar amount of PPCL-Ma-3 is substituted for the PGCL-Ma-3 above but otherwise the procedure is the same.

EXAMPLE IV

PGCL-Ma-3 and dextran-maleic acid monoester (weight ratio of 1:1) are dissolved in dimethyl formamide to provide a concentration of 5% w/v. Then the same photoinitiator as in Example III is added (4% by weight of said resulting reaction product). Then directly before photocrosslinking, 2.5% by weight indomethacin (based on the weight of said resulting reaction product) is added. The resulting composition is poured onto glass plates and irradiated with 365 nm long wave UV lamp for 5 hours. The resulting hydrogel entrapping indomethacin is dried in vacuo at room temperature.

When a vascular stent is substituted for a glass plate, hydrogel with indomethacin entrapped therein is formed on the stent. The coated stent deployed after angioplasty is associated with reduced inflammation compared to a conventional stent.

In another case, an equimolar amount of PPCL-Ma-3 is substituted for the PGCL-Ma-3 above but otherwise the procedure is the same.

EXAMPLE V

PGCL-Ma-3 (1.98 grams), acrylic acid (3.0 grams), and 2,2'-azobisisobutyronitrile (AIBN) in amount of 1.1% by weight of the acrylic acid, are dissolved in 20 ml dioxane at room temperature. The resulting solution is heated to 60° C. for 5 hours. After removal of most of the solvent by distillation at 120° C., the reaction mixture is precipitated in cold water to obtain separation from acrylic acid homopolymer by-product. The precipitate, denoted PGCLA, is filtered, washed with cold water three times and dried oven $P_2O_5$ under vaccum at room temperature.

PGCLA (1.14 grams) is dissolved in 20 ml dioxane at 50° C. and 0.285 grams of N,N'-carbonyl diimidazole is added. After 15 minutes 0.314 grams g 4-amino-2,2,6,6-tetramethyl piperidine-1-oxy (TEMPAMINE) dissolved in 5 ml dioxane is added slowly to the reaction mixture at 50° C. The reaction mixture is vigorously stirred for several hours at 50° C. The resulting solution is added dropwise into petroleum ether to precipitate product where hydroxyl moiety of carboxyl groups of PGCLA is replaced with imino linked to the four position of 2,2,6,6-tetramethylpiperidine-1-oxy, denoted TAM-PGCLA.

A vascular stent is dip coated with TAM-PGCLA by dipping it in a solution of TAM-PGCLA in dioxane (1 gm TAM-PGCLA in 20 ml dioxane) or other suitable solvent and evaporating the solvent. The TAM-PGCLA coated stent deployed after angioplasty is associated with reduced inflammation compared to a conventional stent.

In another case, an equimolar amount of PPCL-Ma-3 is substituted for the PGCL-Ma-3 for the above preparation.

Variations

Many variations of the above will be obvious to those skilled in the art. Therefore the invention is defined by the claims.

What is claimed is:

1. Biodegradable polyhydric alcohol esters where the acyl moieties of the esters originate from aliphatic homopolymer or copolymer polyesters and contain free hydroxyl at their terminal ends, and where the weight average molecular weight of the esters ranges from 1,000 to 80,000.

2. The biodegradable polyhydric alcohol esters of claim 1 where the acyl moieties of the esters originate from polymerization of ε-caprolactone monomer or a blend of ε-caprolactone monomer and lactide monomer or glycolide monomer.

3. The biodegradable polyhydric alcohol esters of claim 1 where the acyl moieties of the esters originate from polymerization of ε-caprolactone monomer.

4. The biodegradable polyhydric alcohol esters of claim 1 where some or each of the acyl moieties are functionalized to incorporate an unsaturated group.

5. The biodegradable polyhydric alcohol esters of claim 4 where the functionalizing is effected by reaction with some or each of the free hydroxyls to provide unsaturated terminal moieties which are 2-carboxy ethenyl groups.

6. The biodegradable polyhydric alcohol esters of claim 5 where unsaturated terminal moieties are reacted with unsaturated carboxyl group containing compound or polymer to provide end segments with a plurality of carboxyl groups thereon.

7. The biodegradable polyhydric alcohol esters of claim 6 where some or each of the carboxyl groups are modified to provide a moiety containing an aminoxyl-containing radical or a moiety comprising other drug molecule residue or other biologically active agent residue, in place of hydroxyl moiety of carboxyl group, to provide a polymer drug delivery and/or release system.

8. The biodegradable polyhydric alcohol esters of claim 1 where the alcohol moieties of the polyhydric alcohol esters originate from polyhydric alcohols containing from 3 to 6 hydroxyl groups.

9. The biodegradable polyhydric alcohol esters of claim 8 where the alcohol moieties of the polyhydric alcohol esters originate from glycerol.

10. The biodegradable polyhydric alcohol esters of claim 8 where the alcohol moieties of the polyhydric alcohol esters originate from pentaerythritol.

11. A biodegradable polyester-polysaccharide hydrogel formed by photocrosslinking unsaturated reaction product formed by reaction of hydroxy of polysaccharide, with 2-carboxy ethenyl group of ester of claim 5.

12. The biodegradable polyester-polysaccharide hydrogel of claim 11 where the polysaccharide is dextran.

13. Drug delivery system comprising the biodegradable hydrogel of claim 12 entrapping or covalently bonded to drug or other biologically active agent to be delivered.

14. A vascular stent containing coating comprising the drug delivery system of claim 13.

15. A vascular stent containing coating comprising the drug delivery and/or release system of claim 7.

* * * * *